(12) United States Patent
Dubnack et al.

(10) Patent No.: US 7,527,624 B2
(45) Date of Patent: May 5, 2009

(54) ELECTRICAL PROBE FOR MICROSURGERY

(75) Inventors: Steffen Dubnack, Jena (DE); Dirk Preuss, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 488 days.

(21) Appl. No.: 11/096,414

(22) Filed: Mar. 31, 2005

(65) Prior Publication Data

US 2006/0069386 A1 Mar. 30, 2006

(30) Foreign Application Priority Data

Apr. 7, 2004 (DE) .................... 10 2004 017 744
Mar. 24, 2005 (DE) .................... 10 2005 013 714

(51) Int. Cl.
*A61B 18/18* (2006.01)

(52) U.S. Cl. ............... 606/41; 606/50; 606/15; 606/4

(58) Field of Classification Search ............ 606/32–35, 606/41, 48–50, 2, 3, 10–15
See application file for complete search history.

(56) References Cited

U.S. PATENT DOCUMENTS

| 4,658,819 | A | * | 4/1987 | Harris et al. ............. 606/34 |
| 4,768,858 | A | * | 9/1988 | Hussein ................. 385/118 |
| 5,383,874 | A | * | 1/1995 | Jackson et al. ............. 606/1 |
| 5,458,597 | A | * | 10/1995 | Edwards et al. ............ 606/41 |
| 5,716,320 | A | * | 2/1998 | Buttermore ............. 600/104 |
| 6,135,998 | A | | 10/2000 | Palanker |
| 6,723,094 | B1 | * | 4/2004 | Desinger ................. 606/50 |
| 6,749,603 | B2 | * | 6/2004 | Dubnack et al. ............ 606/13 |
| 2002/0062126 | A1 | | 5/2002 | Lewis et al. |
| 2004/0199157 | A1 | | 10/2004 | Palanker et al. |

FOREIGN PATENT DOCUMENTS

| DE | 43 39 049 | 5/1995 |
| DE | 195 42 955 | 5/1997 |
| DE | 101 18 464 | 10/2002 |
| DE | 102 49 674 | 5/2004 |
| EP | 1 044 654 | 10/2002 |
| WO | 00/36985 | 6/2000 |

* cited by examiner

*Primary Examiner*—Michael Peffley
(74) *Attorney, Agent, or Firm*—Reed Smith LLP

(57) ABSTRACT

In order to develop an electric probe for microsurgery, which is provided in particular in ophthalmology for intraocular treatments of the eye, in such a way that the probe is constructed in a simple manner, can be produced inexpensively, is easy and safe to handle, and at the same time can be used for multiple functions as an illuminated intraocular probe, it is suggested that the electric probe comprises an outer electrode, an inner electrode and a light guide. The inner electrode has a contoured electrode end face and projects out over a front end of the light guide or is embedded in the light guide so as to terminate with it. When the electrodes and light guide are constructed cylindrically, the hollow space remaining between the electrodes and the light guide is provided as a suction channel for sucking out tissue particles, and in various embodiment forms, including an embodiment as an illuminating endoprobe, the electric probe is connected to an operating and controlling device by which pre.-defined, changeable parameter sets which are adapted depending on the probe characteristics can be adjusted and retrieved.

10 Claims, 4 Drawing Sheets

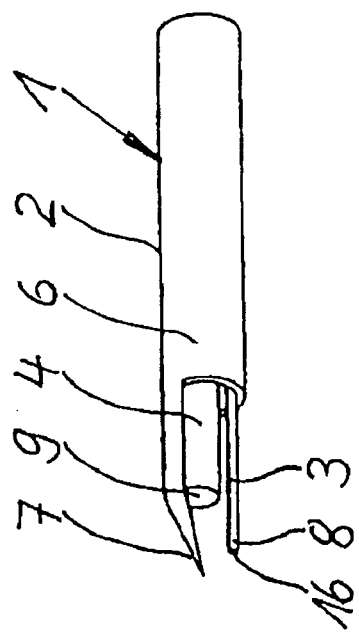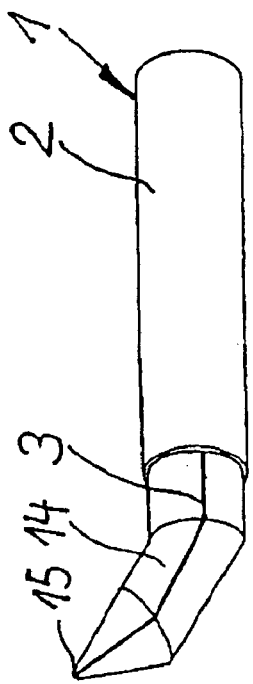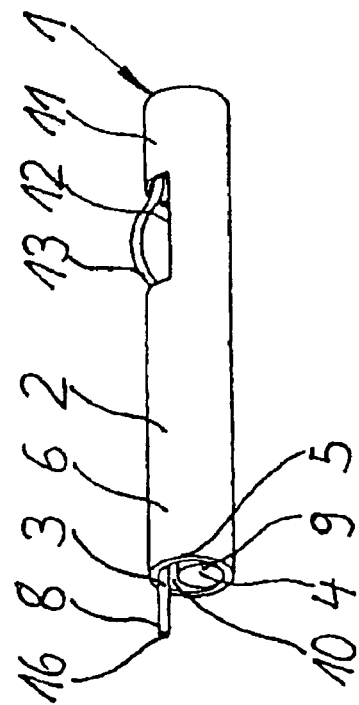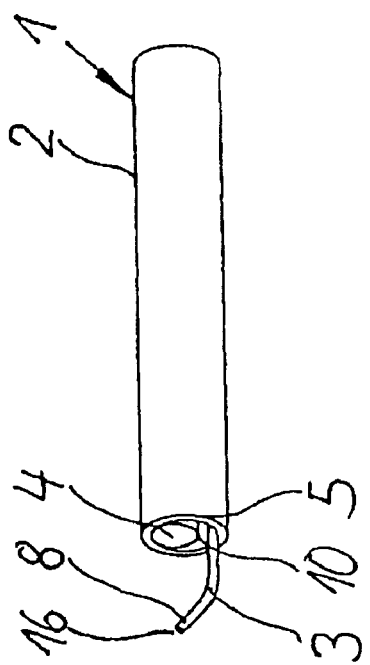

ELECTRICAL PROBE FOR MICROSURGERY

CROSS-REFERENCE TO RELATED APPLICATIONS

This application claims priority of German Application No. 10 2004 017 744.9 filed Apr. 7, 2004 and German Application No. 10 2005 013 714.8, filed Mar. 24, 2005, the complete disclosures of which are hereby incorporated by reference.

BACKGROUND OF THE INVENTION a) Field of the Invention

The invention is directed to an electric probe for microsurgery which is provided in particular in ophthalmology for intraocular treatments of the eye, comprising two electrodes which are arranged coaxial to one another, a light guide which is formed as an insulator preferably being arranged therebetween, wherein the inner electrode and the outer electrode have means for connecting to an operating and controlling device.

b) Description of the Related Art

The use of probes of the kind mentioned above in eye surgery for electrosurgical cutting, ablation or coagulation of tissue is known. When using an electrosurgical probe in surgical operations on the eye, it is problematic to ensure adequate illumination of the interior of the eye or of the fundus of the eye so that illumination is often used in addition to the surgical implement and is guided in through a second puncture. This makes the performance of the operation itself more complicated and also increases stress on and risk to the patent. Another great problem in intraocular treatments of the eye is that currently used cutting implements produce relatively large incisions and the surgeon must move these cutting implements relative to the tissue causing additional tensile and compressive stresses which can lead to unwanted damage to the tissue. Another problem is intraocular illumination. For this reason, probes such as those described in DE 101 18 464 A1 are used to improve the illumination conditions at the operating location of the probe which comprises two electrodes that are connected to a power supply unit and are coaxial to one another, a light guide connected to a light-generating unit being provided between these electrodes.

Further, DE 195 42 955 C2 describes an endoscope with a flexibly constructed cannula whose outer diameter is less than one millimeter and which has light-conducting fibers in the hollow space of the cannula for illuminating the space to be examined and image fibers for transmitting an image of the illuminated space.

U.S. Pat. No. 6,135,998 discloses a method for handling a probe for microsurgery having an inner electrode for use in liquid media. The contour surrounding the inner electrode in the end area at which microplasma threads are formed after an electrical discharge process is constructed of electrically conductive material in a circular or elliptic shape.

Another problem in intraocular treatment of the eye consists in that it is often necessary to detach membranes from one another intraocularly. For this purpose, the membrane to be removed must usually be lifted with forceps and the cutting instrument, e.g., a plasma knife, is introduced between the membrane and the retina in order to detach the synechia or adhesions by plasma cutting. The probe tip itself presents a considerable source of interference in that, on one hand, the electrode tip, when introduced frontally, makes it difficult to carry out lateral ablation between the membrane and retina and, on the other hand, unwanted liquid currents occur that are directed away from the tip. The strength of the currents and the effective depth of the probe shape depend on the electrical energy supplied, so that a destructive action occurs in axial direction and can result in damage to blood vessels or blood-conducting surface capillaries.

OBJECT AND SUMMARY OF THE INVENTION

It is the primary object of the invention to develop an electric probe for microsurgery in such a way that the probe is constructed in a simple manner, can be produced inexpensively, is easy and safe to handle, and at the same time can be used for multiple functions as an illuminated intraocular probe.

This object is met according to the invention in that the electric probe comprises an outer electrode, an inner electrode and a light guide, wherein the inner electrode has a contoured end face and projects out over a front end of the light guide or is embedded therein so as to terminate with it, and wherein the hollow space remaining between the electrodes and the light guide when the electrodes and light guide are constructed cylindrically is provided as a suction channel for sucking out tissue particles.

In an advantageous embodiment form, the inner electrode which is constructed as a hollow body projects out over the front end of the light guide so as to be exposed, wherein a hollow space of the inner electrode can be used as a suction channel.

In another advantageous embodiment form, the light guide is constructed as a hollow body for insulating between the outer electrode and inner electrode, e.g., in the form of a glass rod which surrounds the inner electrode and, at the same time, insulates it from the outer electrode.

It is necessary that there be a minimum distance between the circular inner electrode—which is in the micrometer range—and the end of the outer electrode in order to prevent sparking in the working position.

The outer electrode of the electric probe is preferably formed as a bare metal or partially insulated hollow cylinder enclosing the light guide and the electrically conducting, axially insulated inner electrode which is constructed as a coated wire in particular, and whose front end is bare metal.

In a preferred further development, the inner electrode and the light guide surrounding it together form a free portion which projects from the outer electrode and, in a working position, is covered from above by a cylindrical jacket which narrows conically proceeding from a front side of the outer electrode, in particular to form a tip, and wherein the tip of the outer electrode curves downward or is constructed so as to be bendable so as to project over the free area of the inner electrode and of the light guide.

This construction of the outer electrode makes it possible to detach membranes from one another intraocularly more easily because the membrane to be removed can be lifted by the outer electrode tip so that the adhesions can be detached from one another by microplasma cutting by means of the inner electrode which is inserted between the membrane and the retina.

In a preferred variant, the inner electrode and the light guide, extending separately from one another and parallel to one another, project out of the outer electrode by different distances and, in the working position, are covered from above by the cylindrical jacket proceeding to a tip from the front side of the outer electrode. The inner electrode must project out sufficiently far over the front end of the light guide, preferably by up to one millimeter, or must be at a distance from the location at which at least 75% of the light power exits from the light guide.

In another embodiment form, the light guide and the inner electrode, whose front ends terminate in a flush manner, project together out of the outer electrode so as to form a free portion.

In an equally advantageous embodiment form, the front end of the light guide terminates flush with the front side of the surrounding outer electrode, wherein the inner electrode, projecting from the light guide and the outer electrode, forms a free portion which is constructed in particular so as to curve upward.

In an embodiment form which is advantageous in some cases, the light guide is formed in particular so as to terminate in a tip and, projecting from the outer electrode, is constructed as a glass capillary containing the wire-shaped inner electrode, wherein the inner electrode projects out in particular over the tip of the glass capillary without insulation.

In a particularly advantageous further development, the outer electrode is constructed so as to be displaceable relative to the front end of the inner electrode such that the inner electrode is covered when puncturing the eye and is exposed in the working position, so that working with the electric probe is simpler and easier for the user and unwanted damage of the probe and injury to the eye when inserting the electric probe into the eye are substantially prevented. The displacement of the outer electrode relative to the inner electrode is preferably translational or is carried out by a screwing movement around the inner electrode.

In an advantageous construction that is favorable in technical respects relating to manufacture, the cylindrical jacket of the outer electrode has an opening in its upper area at the end in which a handle is arranged for carrying out the displacement of the outer electrode.

In an advantageous further development, the emitting end of the light guide is constructed conically in particular.

In another preferred further development, a contour of an end face of the inner electrode from which the microplasma filaments proceed is formed of electrically conductive material not over its entire surface, but circularly in particular.

Alternatively, the contour of the electrode end face of the inner electrode can also be formed of electrically conductive material over its entire surface, particularly as a rectangle, line shape or sickle shape or has another contour depending upon application. This surface shaping of the electrode end face of the inner electrode and a suitable choice of electrode corresponding to the different embodiment examples for the specific application ensures that the electric probe can be guided axially during an operation so that certain incisions can be carried out without movements relative to the tissue. This increases safety in achieving suitable miniature incisions.

In other preferred embodiment forms of the electric probe, the electric probe is constructed as an illuminating probe with a scattering surface and an enlarged light exit face, wherein the light guide which surrounds the inner electrode and insulates from the outer electrode projects out of the outer electrode together with the inner electrode so as to form a free portion which ends at a minimum distance in front of the operating area of the inner electrode, and wherein the front end of the inner electrode projects out of the free portion of the light guide. The light exit location preferably narrows conically or narrows cylindrically and conically in direction of the front end of the inner electrode, and the light guide is polished over the entire projecting surface so that light can exit in a diffuse manner over this surface.

In other advantageous embodiment forms, the electric probe has a ring of light waveguides which is provided coaxial to the light guide, wherein the end faces of the annular light waveguides are truncated, in particular so that the operating field is illuminated by the light guide and light waveguide.

Further, for an improved optimal illumination of the operating field, the outer electrode has light exit apertures in its front area, wherein the light exit apertures are constructed as individual openings or as larger light exit surfaces, and wherein a changeable color temperature of the light is preferably provided.

It is essential to the different novel embodiment forms of the electric probe that they have a simple construction and can be produced inexpensively, for example, by means of pre-manufactured insulators of plastic with metal conducting foils and that the outer electrode is constructed as a hollow electrode which can be exchanged by the user after using, is easy and safe to handle and can be used in an all-purpose manner in that a plurality of extensive functions for intraocular treatment of the eye, such as lifting, detaching and removing membranes and making axial incisions, can be carried out with the illuminated intraocular electric probe and the user need not use different probes in the same operation as was customary.

Further advantages of the electric probe according to the invention consist in that a hollow space is formed in the electric probe by the cylindrical construction of the electrodes and of the light guide and is provided for sucking out tissue particles. In addition, operating reliability when working with the electric probe is increased by the embodiment form of an outer electrode which is constructed so as to be displaceable relative to the inner electrode because the inner electrode is only exposed in the working position after insertion into the eye.

The inventive construction of the electric probe as an illuminated endoprobe has the advantage that the operating field is illuminated in an optimal manner due to the arrangement and construction of the light outlet location of the probe and, in addition, a desired color temperature can be adjusted.

In order to further improve handling of the electric probes, the probe is connected to an operating and controlling device in such a way that pre-defined, changeable parameter sets for the probe which are adapted depending on the probe characteristics can be adjusted and retrieved, wherein a sufficient illumination of the operating field is ensured regardless of the working distance, that the operating parameters are regulated through feedback of measurement signals of the electric probe in that the electric probes have output-side coding for detecting the differently constructed probes when the probes are changed, and in that an automatic resetting of the operating parameters occurs when the probes are changed. In addition, the operating and controlling device connected to the electric probe is connected to a multifunction footswitch for working in the operating room so that the individual parameter sets for the probe can be selected by a user by means of a switching movement at the footswitch. In addition, the cutting frequency can be controlled by means of the footswitch. Operation parameters, such as voltage, burst length and burst repetition rate, are advantageously regulated by appropriately predetermined characteristic fields, wherein a user either carries out manual resetting or an automatic resetting of the operating parameters is carried out detection of coded probes or by feedback of measurement signals of the electric probe.

Through the connection of the probe to the operating and controlling device, specific parameter sets (voltage, burst length, burst repetition rate) that are optimized for the treatment area, e.g., for cutting and coagulation of tissue, are preset by means of the control elements operated by the user, either by means of buttons at the operating and controlling device or by means of a switching movement of a footswitch that is connected to the latter. A feedback of the probe to the operating and controlling device is also provided by means of online monitoring of the operating state. A push button of the operating and controlling device is used for gradual adjustment of the intensity of the light.

The invention will be described more fully in the following with reference to embodiment examples that are shown schematically in the drawings.

BRIEF DESCRIPTION OF THE DRAWINGS

In the drawings:

FIGS. 3 to 11 show a full view of other embodiment examples of the electric probe.

DESCRIPTION OF THE PREFERRED EMBODIMENTS

Figure 1:
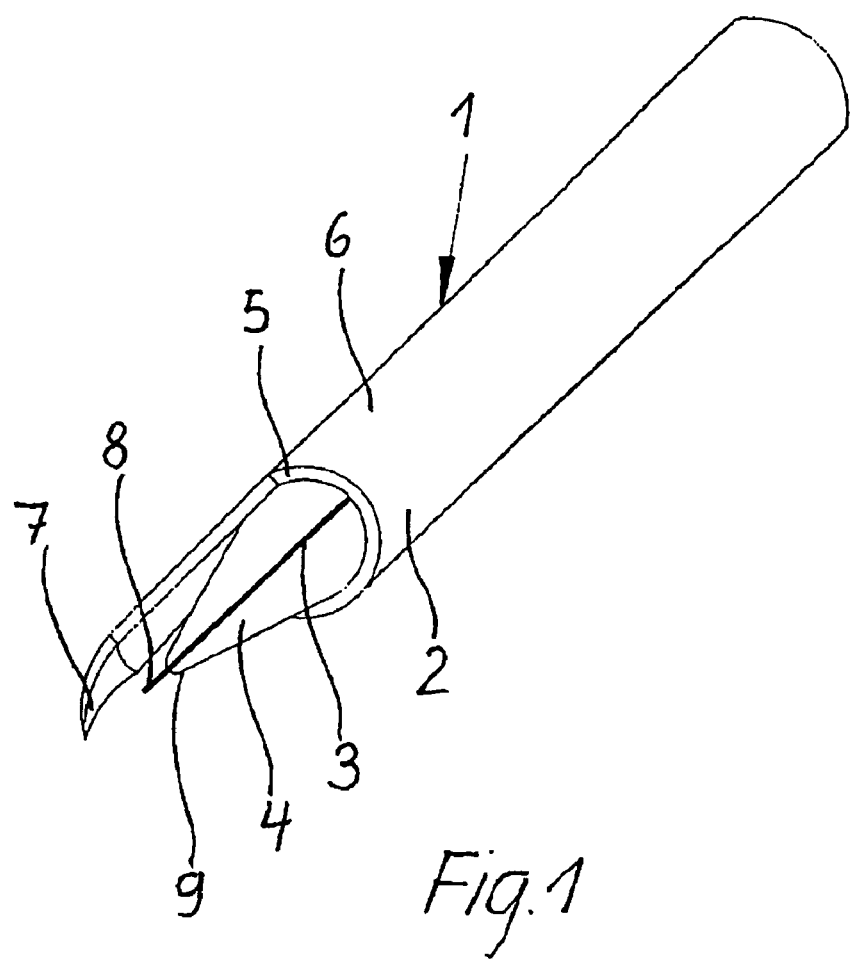
FIG. 1 shows a full view of a first embodiment example of an electric probe according to the invention.

The illuminated intraocular electric probe 1 shown in FIG. 1 comprises a bare metal or partially insulated outer electrode 2 shaped as a hollow cylinder and an electrically conductive, axially insulated inner electrode 3 arranged coaxial to the outer electrode 2. The inner electrode 3 which is provided as a coated wire is constructed within the μm range. A light guide 4 enveloping the inner electrode 3 is arranged between the outer electrode 2 and the inner electrode 3, is constructed as a hollow cylinder and serves to conduct light and as insulate between the outer electrode 2 and inner electrode 3, and is provided, e.g., in the form of a glass rod or a glass capillary 14 which encloses the inner electrode and, at the same time, insulates it from the outer electrode and which is connected when working with the electric probe 1 to a light-generating unit, not shown in more detail.

In the first embodiment example of the electric probe 1 shown in FIG. 1, the inner electrode 3 and the light guide 4 surrounding it project together from a cylindrical jacket 6 of the outer electrode 2 and form a free portion which is covered in the working position by a cylindrical jacket 6, which narrows conically proceeding from a front side 5 of the outer electrode 2, in particular narrows to a tip, such that the tip 7 of the outer electrode 2 is curved downward or is constructed so as to be bendable and projects over the free portion of the inner electrode 3 and of the light guide 4. The end of the tip 7 of the outer electrode 2 can be constructed so as to be slightly curved, for example, for better lifting of the membranes of an eye, for scraping, or for detaching adhesions. The front end 8 of the inner electrode 3, which is exposed to an electrical discharge process for generating microplasma filaments and is surrounded by an electrically conductive liquid, is likewise curved to a tip and is constructed in such a way that the front end 8 of the inner electrode 3 projects without insulation out of a front end 9 of the light guide 4. The front end 9 of the light guide 4 must be at a distance of at least 3 mm from the front side 5 of the outer electrode 2.

Figure 2:
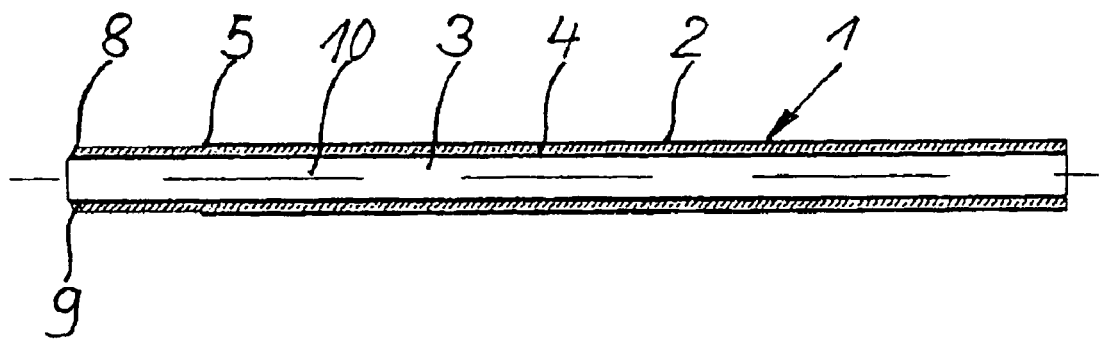
FIG. 2 shows a full view of a second embodiment example of the electric probe in section.

FIG. 2 shows an embodiment example of the electric probe 1 in which the outer electrode 2, the inner electrode 3 and the light guide 4 are constructed as hollow bodies and the hollow space of the inner electrode 3 can be used as a suction channel 10 for sucking out tissue particles. In this embodiment example, the front end 9 of the light guide 4 terminates flush with the front end 8 of the surrounding inner electrode 3. The emitting end of the light guide 4 is cut off perpendicular to the light conducting direction in the light guide 4. However, the emitting end of the light guide 4 can also be spherical, conical or can have another shape.

FIGS. 3 to 11 show other embodiment examples.

FIG. 3 shows an electric probe 1 in which the front end 9 of the light guide 4 terminates flush with the front side 5 of the outer electrode 2 which is formed as a hollow cylinder, and the front end 8 of the inner electrode 3, which is preferably formed as a coated wire, projects out of the front side 5 of the outer electrode 2. The outer electrode 2 is displaceable relative to the free end of the inner electrode 3 so that the inner electrode 3 is covered in the normal position when inserting into the eye and is exposed only in the work position. The displacement, not shown in more detail, can be translational or can be carried out by means of a screwing movement around the inner electrode 3. For displacement of the outer electrode 2, the cylindrical jacket 6 of the outer electrode 2 has an opening 12 in its upper end area 11 in which a narrow, curved handle 13 is provided for initiating the displacement of the inner electrode 3. Because of the cylindrical shape of the electrodes 2, 3 and of the light guide 4, the cross section left over between the electrodes 2, 3 and the light guide 4 can be used as a suction channel 10 for sucking out tissue particles.

FIG. 4 shows another embodiment example of the electric probe 1 in which the inner electrode 3 projects out of the outer electrode 2 which is formed as a hollow cylinder. The front end 8 of the inner electrode 3 is curved upward and the light guide 4 terminates flush with the front side 5 of the outer electrode 2.

The embodiment form of the electric probe 1 shown in FIG. 5 comprises the outer electrode 2 which is formed as a hollow cylinder. The inner electrode 3 which is constructed as a coated wire and the light guide 4 project out of the cylindrical jacket 6 of the outer electrode 2 by different distances so as to extend parallel to one another and are covered by the tip 7 projecting from the front side 5 of the outer electrode 2. The front end 8 of the inner electrode 3 projects out of the hollow cylinder of the outer electrode 2 farther than the cylindrically shaped light guide 4.

FIG. 6 shows a special embodiment form of the electric probe 1 as a shaped electrode in which the outer electrode 2 is likewise formed as a hollow cylinder from which an upwardly curved inner electrode 3 projects. The inner electrode 3 is enclosed by a glass capillary 12 exercising the function of light guide 4 and terminating in a tip 13. In other embodiment forms of the electric probe 1 which are not shown, the contour of the electrode end face 16 of the inner electrode 3 from which the microplasma filaments proceed is not formed of electrically conducting material over its entire surface, in particular, is constructed as a hollow electrode, and the other surfaces of the inner electrode 3 are insulated. The contour of the electrode end face 16 of the inner electrode 3 is circular in particular.

Alternatively, the contour of the electrode end face 16 of the inner electrode 3 is formed of electrically conductive material over its entire surface and has a rectangular, line-shaped, sickle-shaped or other contour depending upon application.

In another embodiment form of the electric probe 1 which is not shown, the outer electrode 2 and the inner electrode 3 are constructed as electrode cannulas, and the inner, fully insulated electrode cannula is provided with a fork-like hook that is bent forward around the electrode tip and whose bent end is not insulated.

Figure 7:
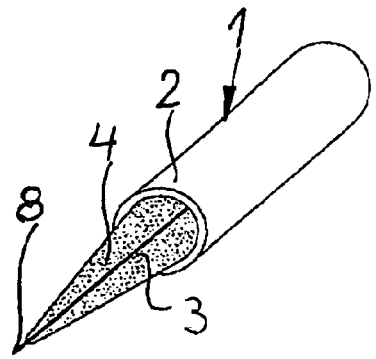
Figure 8:
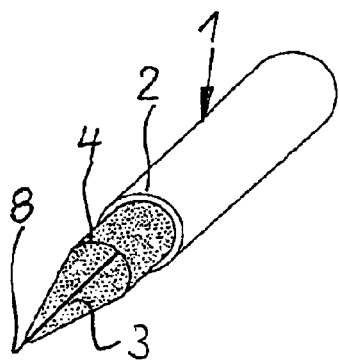

FIGS. 7 and 8 show two embodiment examples of the electric probe 1 with an enlarged light exit surface. The outer electrode 2 terminates at least 3 mm in front of the actual working area of the projecting inner electrode 3, and the front end 8 of the inner electrode 3 projects out of the free surface of the light guide 4 which is constructed so as to be polished over the entire projecting surface in order to enable light to exit diffusely over this surface.

Figure 9:
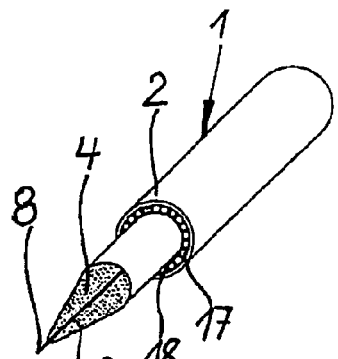

FIG. 9 shows an embodiment example in which the electric probe 1 comprises the outer electrode 2, the coaxial light guide 4 and an additional ring of light waveguides 17. The end faces 18 of the light waveguides 17 are truncated. Accordingly, an operating field can be illuminated through the light guides 4 and, additionally, through the light waveguides 17. The distance between the light exit face, the end faces 18 of the light waveguides 17 and that of the front end of the inner electrode 3 should not be less than 3 mm.

Figure 10:
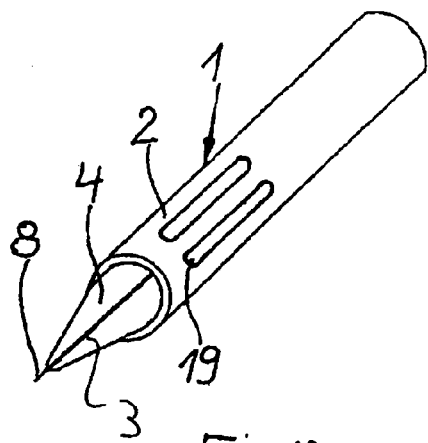
Figure 11:
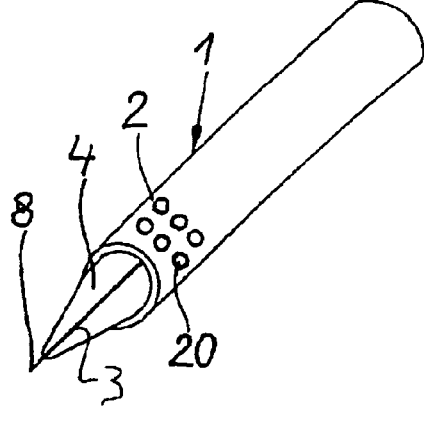

FIGS. 10 and 11 show embodiment examples of the electric probe 1 with the outer electrode 2, the coaxial light guide 4 and the inner electrode 3 embedded therein. The outer electrode 2 is provided in the distal area with light exit apertures 19, 20. These openings 19, 20 are shown only schematically in FIGS. 10 and 11; they can also have a larger surface or other geometries. A suitable treatment of the light guide surface or insulator surface is a prerequisite for light output. The advantage of this arrangement is that the outer electrode 2 can be brought very close to the operating field and the electrical losses can accordingly be kept small. The light outlet location can be arranged directly behind the working area of the electric probe 1 up to a distance of, e.g., 10 mm behind the end of the probe 1. The surface of the light-conducting light guide 4 can also be so constructed by means of slots or notches or by a rough grinding that the light is emitted laterally at this location.

In an embodiment form, not shown, of the electric probe 1 which is favorable in technical respects relating to manufacture, the handle is constructed with the probe tip or only the probe tip is constructed in such a way that the portion of the electric probe 1 coming into contact with a patient is constructed as a sterile disposable product and the second half of the probe 1 such as a plug, cable and handle can be re-sterilized by a user.

Figure 12:
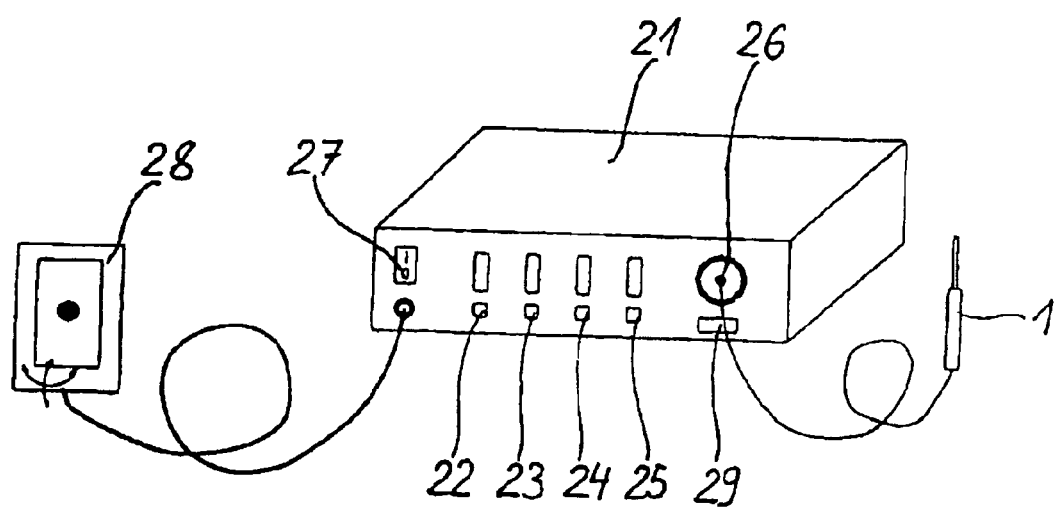
FIG. 12 shows an embodiment example of an operating and controlling device for the electric probe.

FIG. 12 shows the operating and controlling device 21 for an electric probe 1 in the form of a device in which it is possible to set predefined parameter sets for the corresponding treatment area by means of buttons 22, 23, 24, 25. For this purpose, the electric probe 1 is connected to a socket 26 of the operating and controlling device 21 by the doctor before the start of the operation. The operating and controlling device 21 is switched on by means of a button 27 and controlled by a multifunction footswitch 28. The parameter sets can be selected by the doctor by means of buttons 22, 23, 24, 25 and/or by means of a switching movement at the multifunctional footswitch 28. A push button 29 provided at the operating and controlling device 21 is used for gradual adjustment of the intensity of the light. For internal control of parameters, a reaction to a reduction in the jacket surface is proposed by means of continuously adapting the operating parameters such as voltage, burst length and burst repetition rate during the operation of the electric probe 1. This is carried out either by regulating the operating parameters such as voltage, burst length and burst repetition rate in an advantageous manner by previously determined characteristic fields. The user either resets manually or an automatic resetting of the operating parameters is carried out by detection of coded probes or by feedback of measurement signals of the probe.

While the foregoing description and drawings represent the present invention, it will be obvious to those skilled in the art that various changes may be made therein without departing from the true spirit and scope of the present invention.

REFERENCE NUMBERS 1 electric probe
2 outer electrode
3 inner electrode
4 light guide
5 front side of the outer electrode
6 cylindrical jacket
7 tip of the outer electrode
8 front end of the inner electrode
9 front end of the light guide
10 suction channel
11 end area of the cylindrical jacket
12 opening
13 handle
14 glass capillary
15 tip of the glass capillary
16 electrode end face of the inner electrode
17 annular light waveguide
18 end face of the annular light waveguide
19 light exit aperture
20 light exit aperture
21 operating and controlling device
22 button
23 button
24 button
25 button
26 socket
27 button
28 multifunction footswitch
29 push button

The invention claimed is:

1. An electric probe for microsurgery which is provided in particular in ophthalmology for intraocular treatments of the eye, comprising:
   two electrodes which are arranged where one electrode lies within the other, said electrodes comprising an inner electrode and an outer electrode;
   a light guide which is formed as an insulator being arranged therebetween;
   said inner electrode and said outer electrode having means for connecting to an operating and controlling device for the electric probe;
   said inner electrode further having a contoured electrode end face and is embedded in the light guide;
   wherein the light guide is constructed as a hollow body for insulating between the outer electrode and inner electrode, wherein the light guide is constructed in particular as a glass rod which surrounds the inner electrode and, at the same time, insulates the inner electrode from the outer electrode; and
   wherein the emitting front end of the light guide is constructed conically in particular.

2. The electric probe according to claim 1,
   wherein the inner and outer electrodes are coaxial with each other.

3. The electric probe according to claim 1,
wherein the light guide and the inner electrode, whose front ends terminate in a flush manner, project together out of the outer electrode so as to form a free portion.

4. The electric probe according to claim 1,
wherein the light guide is formed in particular so as to terminate in a tip and, projecting from the outer electrode, is constructed as a glass capillary containing the inner electrode, and
wherein the inner electrode projects out in particular over the tip of the glass capillary without insulation.

5. The electric probe according to claim 1,
wherein the electric probe is constructed as an illuminating probe with a scattering surface, wherein the inner electrode and the light guide surrounding the inner electrode project together out of the outer electrode so as to form a free portion which ends at a minimum distance in front of the operating area of the inner electrode, and
wherein the front end of the inner electrode projects out of the light guide portion of the free portion.

6. The electric probe according to claim 5,
wherein the free portion of the light guide narrows conically in direction of the front end of the inner electrode and is polished so that light can exit in a diffuse manner.

7. The electric probe according to claim 5,
wherein the free portion of the light guide is constructed so as to narrow cylindrically and conically in direction of the front end of the inner electrode.

8. The electric probe according to claim 5,
wherein a ring of light waveguides is arranged coaxial to the light guide between the light guide and the outer electrode,
wherein the end faces of the annular light waveguides are truncated in particular, and
wherein a minimum distance is given between the light exit face of the annular light waveguide and the front end of the inner electrode.

9. The electric probe according to claim 5,
wherein the outer electrode has light exit apertures in its distal front area, and
wherein the light exit apertures are constructed as individual light exit apertures or as a larger light exit surface, and a changeable color temperature of the light is provided.

10. The electric probe according to claim 1,
wherein the inner electrode is embedded in the light guide so as to terminate with it.

\* \* \* \* \*